United States Patent [19]
Olsson et al.

[11] Patent Number: 5,918,595
[45] Date of Patent: Jul. 6, 1999

[54] METHOD FOR VAPORIZING AN ANESTHETIC LIQUID AND VAPORIZER OPERATING ACCORDING TO THE METHOD

[75] Inventors: Sven-Gunnar Olsson, Arlöv; Göran Rydgren, Bunkeflostrand; Anders Larsson, Kävlinge; Tarmo Niininen, Höör, all of Sweden

[73] Assignee: Siemens-Elema AB, Solna, Sweden

[21] Appl. No.: 08/771,226

[22] Filed: Dec. 20, 1996

[30] Foreign Application Priority Data

Dec. 21, 1995 [SE] Sweden .................................. 9504580

[51] Int. Cl.⁶ .......................... B01D 47/02; A61M 16/18; A61M 16/00
[52] U.S. Cl. .............................. 128/203.26; 128/203.16; 128/203.12; 261/DIG. 65; 261/30; 261/121.1
[58] Field of Search ......................... 128/200.11, 203.26, 128/203.27, 203.12, 203.16; 261/30, 18.2, 121.1, DIG. 65

[56] References Cited

U.S. PATENT DOCUMENTS

| | | |
|---|---|---|
| 3,593,710 | 7/1971 | Eichelman et al. ............... 128/200.11 |
| 3,794,027 | 2/1974 | Johnson . |
| 4,276,243 | 6/1981 | Partus ...................................... 261/128 |
| 4,436,674 | 3/1984 | McMenamin ........................ 261/64 B |
| 4,750,483 | 6/1988 | Ankartross et al. ............... 128/203.26 |
| 5,065,753 | 11/1991 | Kalishman ........................ 128/200.11 |
| 5,693,189 | 12/1997 | Oguro et al. .................................. 203/3 |

FOREIGN PATENT DOCUMENTS

| | | |
|---|---|---|
| 0 166 305 | 1/1986 | European Pat. Off. . |
| 0 454 390 | 10/1991 | European Pat. Off. . |
| 0 496 336 | 7/1992 | European Pat. Off. . |
| 41 05 971 | 8/1992 | Germany . |
| 41 07 061 | 9/1992 | Germany . |
| 631577 | 11/1949 | United Kingdom .............. 128/200.11 |
| WO 92/19303 | 11/1992 | WIPO . |

OTHER PUBLICATIONS

Patent Abstract of Japan, vol. 14, No. 53 (C–683) for application No. 63–107590, Nov. 1989.
Excerpt from Operating Manual for Siemens Elema Vaporizer Models 950, 951 and 952 (1988) 3 pgs.

*Primary Examiner*—Kimberly L. Asher
*Attorney, Agent, or Firm*—Hill & Simpson

[57] ABSTRACT

In a method an apparatus for vaporizing anesthetic liquids, in which a carrier gas is passed through a vaporizer so as to be saturated with vaporized anesthetic liquid, the vaporizer has a container, partially filled with anesthetic liquid, an inlet for a carrier gas, an outlet for carrier gas saturated with anesthetic and a pressure chamber. The carrier gas is supplied to the vaporizer at a pressure exceeding atmospheric pressure and is bubbled through the anesthetic liquid in the container in order to become saturated with anesthetic. The flow of gas at the outlet can be regulated as needed. Exact pressure and temperature conditions can be measured and/or regulated with a pressure meter, pressure regulator, thermometer and temperature regulator in order to regulate the partial pressure of anesthetic in the container.

19 Claims, 1 Drawing Sheet

METHOD FOR VAPORIZING AN ANESTHETIC LIQUID AND VAPORIZER OPERATING ACCORDING TO THE METHOD

BACKGROUND OF THE INVENTION

1. Field of the Invention

The present invention relates to a method for vaporizing an anesthetic liquid of the type wherein a carrier gas is passed through a container, which is at least partially filled with anesthetic liquid with the carrier gas saturated with vaporized anesthetic being supplied to an anesthetic apparatus for mixture with other gas components to form a breathing gas.

The present invention also relates to a vaporizer of the type operating as generally described above.

2. Description of the Prior Art

The most common way of supplying anesthetic to a patient who is to be anesthetized is to vaporize a specific amount of an anesthetic liquid in a vaporizer, disposed at an anesthetic apparatus, and to deliver this anesthetic in a gas mixture consisting of oxygen and nitrous oxide (and sometimes air) to the patient via the apparatus. Many types of vaporizers are available. The various vaporizers differ in particular in the way in which anesthetic liquid is vaporized and conveyed with the carrier gas. The vaporizer can be located on the low-pressure side of the anesthesia system, in which gas pressure is the pressure to which the patient is subjected, i.e., about atmospheric pressure, or on the high pressure side, in which gas pressure exceeds normal atmospheric pressure, i.e., usually 2 to 6 bars of gauge pressure.

One type of high-pressure vaporizer is described in the brochure "Halothance Vaporizer 950/Enflurane Vaporizer 951/Isoflurane Vaporizer 952"—Operating Manual, AG 0188 7, Siemens-Elema AB, 1988. The anesthetic liquid is in a container on the highpressure side of an anesthetic system. One line carries a relatively large flow of a gas mixture through the vaporizer and on to the anesthetic apparatus. A throttle valve is disposed within the vaporizer and upstream from the throttle valve there is an opening between the line and the container. Downstream from the throttle valve a nozzle is located in the line. The nozzle is connected to a tube immersed in the anesthetic liquid. A pressure drop is caused across the throttle valve due to the flow of the gas mixture through it. As a result of the pressure gradient, anesthetic liquid is pressed out through the nozzle into the lire and is vaporized by the passing flow of breathing gas. The amount of anesthetic liquid to be vaporized is regulated by changing the position of the throttle valve and, accordingly, the magnitude of the drop in pressure. When no anesthetic liquid is to be vaporized, a valve is reset, and the gas mixture bypasses the vaporizer. Since the pressure drop across the throttle valve is also governed by absolute pressure, the vaporizer must be calibrated for an entering pressure, or range of pressures, which may be a source of error. Another possible source of error which must be taken into account with this type of vaporizer is the container's compressible volume and the amount of anesthetic liquid contained in the container.

One type of low-pressure vaporizer is described in European Application 166 305. In this vaporizer, a specific amount of anesthetic liquid is delivered to a hot plate in a vaporizing chamber. A total flow of a gas mixture passes through the vaporizer and conveys the vaporized anesthetic liquid. The amount of liquid sent to the vaporizing chamber is therefore governed by the magnitude of the gas flow and the desired concentration of anesthetic in the gas mixture. Since two factors affect the course of events, the risk of erroneous dosing is increased. Even if such errors are usually not large enough to pose any risk to the patient, they do exist. Moreover, this type of vaporizer is hard to replace while in operation. One version of this type of vaporizer is described in PCT Application WO 92/19303.

Second and third types of low-pressure vaporizers are described in U.S. Pat. No. 3,794,027. The second type of low-pressure vaporizer has a container holding anesthetic liquid. A wick is partially immersed in the liquid. The gas can be carried, via a manually switchable valve, either through or past the low-pressure vaporizer. When gas is sent through the low-pressure vaporizer, it passes the wick which has drawn up anesthetic liquid. Liquid in the wick is vaporized by the passing flow of gas and is carried, with the gas, to the patient. In principle, vaporization is controlled by the physician switching the valve so gas is channeled through the low-pressure vaporizer for specific periods of time. The system's efficacy is therefore completely dependent on the physician's skill and experience.

The third type of low-pressure vaporizer also has a container filled with anesthetic liquid. A flow of gas at a relatively low pressure is connected thereto. The flow of gas is then allowed to bubble through the anesthetic liquid so as to become saturated with vaporized anesthetic liquid. The gas is then carried with anesthetic gas to the anesthetic machine and the patient. As is the case with the second type of low-pressure vaporizer, this type utilizes manual bypass for specific periods of time in regulating the end concentration of anesthetic.

Thus, a problem encountered with most types of anesthetic vaporizers is a lack of accurate control of the amount of anesthetic liquid vaporized. Since the gases are involved, both compression and flow affect the final concentration of anesthetic gas in the breathing gas. As the above shows, different techniques are used in attempts to control the amount of anesthetic liquid to be vaporized. The last vaporizer mentioned, in which breathing gas is saturated with vaporized anesthetic, has the advantage that the anesthetic liquid's partial pressure is well-defined at a given temperature and pressure. This type of vaporizer, however, is riot without problems. Since it is directly connected to the patient circuit in some way, it exhibits a large compressible volume, making control of the amount of anesthetic in the system more difficult. Switching from one anesthetic to another is a complex operation, and there is always a risk of leakage through backflow, and saturation of breathing gas passed through the vaporizer must be assured.

Instead of passing the entire flow of gas through the low-pressure vaporizer, for specific periods of time, to be saturated with anesthetic, a small, exact, partial flow of gas can instead be passed, almost continuously, through the low-pressure vaporizer in order to be saturated with anesthetic. One such design is described in European Application 496 336.

SUMMARY OF THE INVENTION

An object of the present invention is to provide a vaporizer, and a method for operating a vaporizer, wherein the aforementioned problems associated with the prior art are avoided.

The above object is achieved in accordance with the invention in a method for vaporizing an anesthetic liquid wherein a carrier gas as used in the low-pressure vaporizers is employed, but this carrier gas is supplied to the container at a gauge pressure exceeding 0.1 bar.

The carrier gas thus is sent to the vaporizer at a pressure which is relatively high for this context in the anesthetic art. In other words, the high-pressure side is utilized in a new manner. Gas flow from the vaporizer, i.e., carrier gas saturated with anesthetic gas, can be controlled as needed with a valve which increases accuracy immensely when compared with known high-pressure vaporizers. The vaporizer can accordingly be arranged, in principle, independently of the anesthetic apparatus, making it easy to switch from one vaporizer to another. Since the entire vaporizer is located outside the anesthetic apparatus and only has a limited volume, compressible volume is minimized, and the risk of backflow through the vaporizer is virtually non-existent, due to the high pressure on the input side and valve-regulation of flow from the vaporizer to a low-pressure system. Measurement of pressure and temperature makes it possible to achieve exact determinations of the concentration of anesthetic gas.

In versions of the method in accordance with the invention, temperature and/or pressure are/is regulated in different ways. For example, the temperature can be regulated at an exact value at the same time as gauge pressure is varied to regulate the concentration. The advantage of this approach is that a constant flow can be extracted from the vaporizer while the concentration of anesthetic can still be varied.

The above object is also achieved in accordance with the principles of the present invention in a vaporizer designed to be arranged on the high-pressure side of an anesthetic system, the vaporizer having a container for anesthetic liquid, an inlet for a carrier gas, and an outlet for carrier gas saturated with vaporized anesthetic. A pressure chamber at least partially surrounds the container and is connected to the inlet. The pressure chamber is connectable to a high-pressure source for the carrier gas. The analyzer also includes a pressure meter for measuring pressure in the pressure chamber or in the container, and a thermometer for measuring the temperature in the container and/or the temperature of the anesthetic liquid. A control unit calculates the concentration of vaporized anesthetic in the carrier gas at the outlet from the measured pressure and temperature.

DESCRIPTION OF THE PREFERRED EMBODIMENTS

Figure 1:
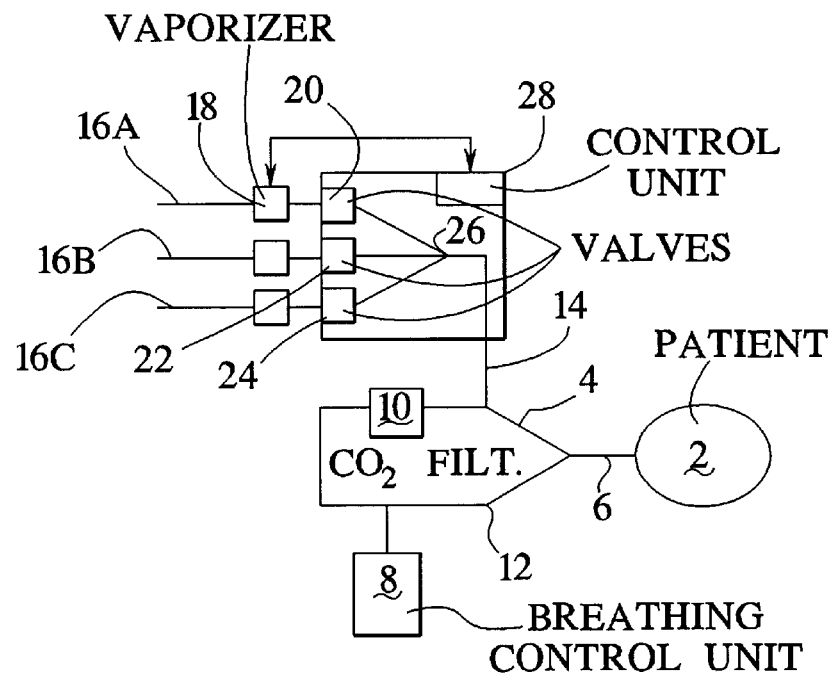
FIG. 1 shows an anesthetic apparatus connected to a patient, with which a vaporizer constructed and operating according to the invention can be used.

FIG. 1 shows a closed anesthetic system with re-breathing of expired breathing gas. A patient 2 is connected to an anesthetic apparatus and receives, via an inspiratory line 4, breathing gas containing anesthetic gas. Gas is carried down into the lungs of the patient 2 through a tracheal tube 6 or the equivalent. The breathing of the patient 2 is regulated by a breathing control unit 8 which can include a manual or mechanical pump, e.g., a so-called bag and bottle. During inspiration, gas passes a carbon dioxide filter 10 which removes carbon dioxide from the gas. During expiration, gas expired by the patient is carried, through the tracheal tube 6 and an expiratory line 12, back to the breathing control unit 8. When a specific gas is consumed by the patient, or leaks out of the system, fresh breathing gas is supplied through a fresh gas line 14. Fresh gas is carried to the anesthetic apparatus through each of a first gas connector 16A, a second gas connector 16B and a third gas connector 16C. The gases could be, for example, oxygen through the first and second gas connectors 16A, 16B and nitrous oxide through the third gas connector 16C.

The first gas connector 16A is connected to a vaporizer 18 located on the high-pressure side of the anesthetic apparatus. An exact quantity of anesthetic liquid is vaporized in the vaporizer 18 for addition to the gas from the first gas connector 16A, this gas accordingly serving as a carrier gas for the vaporized anesthetic. A first valve 20 regulates the flow of carrier gas saturated with vaporized anesthetic liquid. A second valve 22 regulates the flow of gas from the second gas connector 16B and a third valve 24 regulates flow from the third gas connector 16C. The gases from the respective gas connectors 16A, 16B and 16C are mixed in a mixing chamber 26 and the mixture is carried through the fresh gas line 14 to the inspiratory line 4 in the patient circuit. The vaporizer 18 is controlled by a control unit 28. The control unit 28 also controls the valves 20, 22 an 24.

Figure 2:
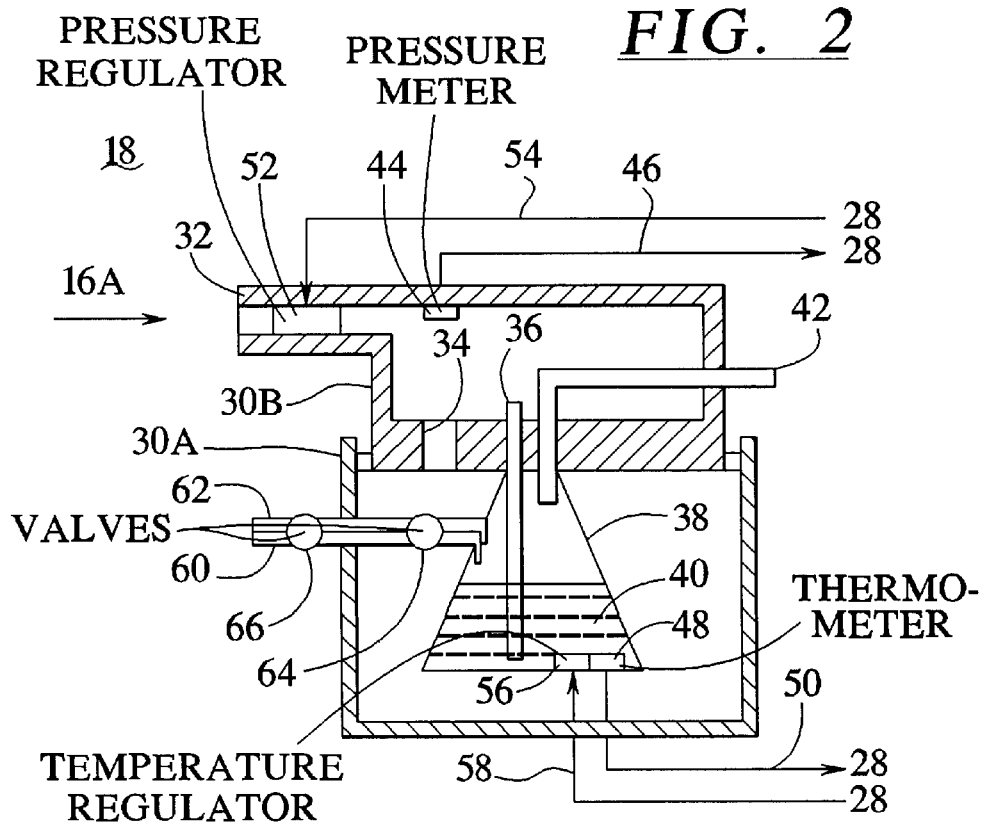
FIG. 2 shows one embodiment of the vaporizer constructed and operating according to the invention.

FIG. 2 shows the vaporizer 18 in greater detail. The vaporizer 18 has a pressure chamber, which is divided into a lower pressure chamber section 30A and an upper pressure chamber section 30B. The pressure chamber sections 30A and 30B are hermetically connected to each other. A pressure equalization opening 34 is arranged between the pressure chamber sections 30A and 30B. High pressure carrier gas is conveyed through a vaporizer inlet 32 from the first gas connector 16A in the upper pressure chamber section 30B at pressures between 0.1 bar and 6.5 bars. A check valve (not shown) can be arranged at the vaporizer inlet 32 to ensure that vaporized anesthetic liquid is kept from passing into the gas connector 16A.

Carrier gas from the gas connector 16 then passes, through an inlet 36, down into a container 38 which is partially filled with an anesthetic liquid 40. The container 38 can suitably be a glass piston, and the lower pressure chamber section 30A can suitably be made of a transparent material. The quantity of anesthetic can then be manually monitored.

Carrier gas bubbles through the anesthetic liquid 40 and is thereby saturated with vaporized anesthetic. Carrier gas, saturated with anesthetic, can then be conveyed through an outlet 42 to the valve 20 (in FIG. 1). A pressure meter 44 is arranged in the upper pressure chamber section 30B to measure a pressure which is effective in the pressure chamber section 30B such as by measuring the actual pressure therein. The pressure meter 44 sends a pressure measurement signal to the control unit 28 via a first signal line 46. In the corresponding manner, a thermometer 48 is arranged in the container 38, such as in the anesthetic liquid 40, to measure the temperature effective on the anesthetic liquid 40. The thermometer 48 sends a temperature measurement signal to the control unit 28 via a second signal line 50. The partial pressure of vaporized anesthetic liquid, and, accordingly, the exact concentration of anesthetic in the carrier gas, can be calculated from the measured pressure and temperature.

The pressure meter 44 can alternatively be arranged by or in the first valve 20 on the high-pressure side.

A pressure regulator 52 is arranged at the inlet 32 to regulate entering pressure in the upper pressure chamber section 30B in order to regulate the concentration or, more accurately, the partial pressure of anesthetic in the vaporizer. The pressure regulator 52 is controlled by the control unit 28 via a third signal line 54. A physician selects an appropriate valve for the concentration of anesthetic gas in the breathing gas supplied to the patient, and a control unit calculates, on the basis thereof, an appropriate reference valve for the pressure of gas in the container 38. The pressure regulator 52 is then regulated, via the control unit 28, until a gas pressure corresponding to the calculated reference value is measured by the pressure meter 44.

The temperature effective on the anesthetic liquid 40 can be regulated in the corresponding manner. Every specific anesthetic liquid should be regulated to a constant temperature specific to that liquid. A temperature regulator 56 is arranged in the anesthetic liquid 40 and is controlled by the control unit 28 via a fourth signal line 58. In the same way as for pressure, a reference value can be set for temperature and then regulated by the control unit, via the temperature regulator 56, until the thermometer 48 measures the desired temperature.

Regulating pressure to keep it on a constant level and then varying the temperature in order to vary the partial pressure and, accordingly, concentration of the anesthetic gas is also possible.

Since the valve 20 is also able to regulate an accurate flow of carrier gas with anesthetic gas, here, is a third way of regulating concentration. If pressure and temperature are regulated at specific, constant values, the concentration of the final gas mixture can be regulated when the percentage of carrier gas plus anesthetic gas in the total gas mixture is varied via the valves 20, 22 and 24.

If pressure and temperature are allowed to vary, compensations for this variation can be made with the valves 20, 22 and 24. These variations must be measured for this to be possible.

Combinations of these regulatory operations, entailing the control of a number of variables, are possible, but regulation will be more reliable and accurate in most instances if only one parameter is varied.

A filler tube 60 and purging tube 62 are arranged at the container 38 to make it easier to fill the container 38 with fresh anesthetic liquid 40. Since the container 38 is pressurized, the tubes 60 and 62 are equipped with a first valve 64 by the container 38 and a second valve 66 on the exterior of the pressure chambers 30A and 30B. The valves 64 and 66 serve as a lock during the filling of anesthetic liquid.

Although modifications and changes may be suggested by those skilled in the art, it is the intention of the inventors to embody within the patent warranted hereon all changes and modifications as reasonably and properly come within the scope of their contribution to the art.

We claim as the invention:

1. A method for vaporizing an anesthetic liquid comprising the steps of:
   at least partially filling a container with anesthetic liquid;
   passing a carrier gas into said anesthetic liquid in said container at a gauge pressure relative to atmospheric pressure exceeding 0.1 bar and thereby saturating said carrier gas with vaporized anesthetic; and
   forming a breathing gas containing said carrier gas saturated with anesthetic and at least one other gas and delivering said breathing gas to a subject.

2. A method as claimed in claim 1 wherein the step of passing said carrier gas through said container is further defined by passing said carrier gas through said container with a gauge pressure relative to atmospheric pressure exceeding 0.5 bar.

3. A method as claimed in claim 1 comprising the additional steps of:
   measuring a pressure in said container;
   measuring a temperature in said container; and
   identifying a concentration of the vaporized anesthetic in the carrier gas from the measured pressure and temperature.

4. A method as claimed in claim 1 comprising the additional steps of:
   measuring a pressure in said container;
   measuring a temperature in the anesthetic liquid; and
   identifying a concentration of the vaporized anesthetic in the carrier gas from the measured pressure and temperature.

5. A method as claimed in claim 1 wherein the step of passing said carrier gas through said container is further defined by passing said carrier gas through said container at a gauge pressure relative to atmospheric pressure in a range between 2 bars and 6.5 bars.

6. A method as claimed in claim 1 comprising the additional steps of:
   regulating a temperature in said container to maintain said temperature in said container at a predetermined constant value; and
   varying said gauge pressure imposed on said carrier gas for regulating a concentration of said vaporized anesthetic in said carrier gas.

7. A method as claimed in claim 1 comprising the additional steps of:
   regulating a temperature of said anesthetic liquid to maintain said temperature in said container at a predetermined constant value; and
   varying said gauge pressure imposed on said carrier gas for regulating a concentration of said vaporized anesthetic in said carrier gas.

8. A method as claimed in claim 1 comprising the additional step of:
   regulating a flow of said carrier gas saturated with vaporized anesthetic from said container for maintaining a predetermined concentration of said anesthetic in said breathing gas.

9. A method as claimed in claim 1 wherein the step of passing said carrier gas through said container includes bubbling said carrier gas through said anesthetic liquid.

10. A vaporizer for use with an anesthetic system having a high-pressure side, said vaporizer comprising:
    a container at least partially filled with anesthetic liquid, said container having an inlet and said container having an outlet connectable to said high-pressure side of said anesthetic system;
    a pressure chamber at least partially surrounding said container and connected to said inlet;
    a high-pressure source of carrier gas connected to said pressure chamber, said carrier gas being forced through said container and becoming saturated with anesthetic liquid and exiting said container at said outlet;
    a pressure meter which measures a pressure effective in said pressure chamber;
    a thermometer which measures a temperature effective on said anesthetic liquid; and
    control means for calculating a concentration of vaporized anesthetic in said carrier gas at said outlet from the measured pressure and temperature.

11. A vaporizer as claimed in claim 10 wherein said pressure meter is disposed in said container.

12. A vaporizer as claimed in claim 11 further comprising pressure regulator means for regulating said pressure in said container.

13. A vaporizer as claimed in claim 10 wherein said pressure meter is disposed in said pressure chamber.

14. A vaporizer as claimed in claim 13 further comprising pressure regulator means for regulating said pressure in said pressure chamber.

15. A vaporizer as claimed in claim 10 wherein said thermometer is disposed in said container.

16. A vaporizer as claimed in claim 15 further comprising temperature regulator means for regulating the temperature in said container.

17. A vaporizer as claimed in claim 10 wherein said thermometer is disposed in said anesthetic liquid.

18. A vaporizer as claimed in claim 17 further comprising temperature regulator means for regulating the temperature of said anesthetic liquid.

19. A vaporizer as claimed in claim 10 further comprising a filler lock connecting an interior of said container to an exterior of said pressure chamber, said filler lock having a first valve disposed between said interior of said container and a volume in said filler lock, and a second valve communicating between said exterior of said pressure chamber arid said volume of said filler lock.

* * * * *